United States Patent [19]

Manis

[11] 4,273,875
[45] Jun. 16, 1981

[54] PLASMID AND PROCESS OF ISOLATING SAME

[75] Inventor: Jack J. Manis, Portage, Mich.

[73] Assignee: The Upjohn Company, Kalamazoo, Mich.

[21] Appl. No.: 17,812

[22] Filed: Mar. 5, 1979

[51] Int. Cl.³ .............................................. C12N 1/20
[52] U.S. Cl. ...................................... 435/253; 435/91; 435/317; 435/820; 435/886
[58] Field of Search .................. 435/91, 317, 820, 253

[56] References Cited
PUBLICATIONS

J. Gen. Microbiol 106, 377–381, 201–206 (1978).
J. Gen. Microbiol 79, 331–342 (1973).
J. Antibiotics 30, 1146–1149, 897–899 (1977).
Nature 254, 265–267 (1975).
J. Gen. Microbiol 98, 239–252 (1977).
J. Antibiotics 33, 45–47 (1969).
Broda, Plasmids, Freeman and Company Ltd., p. 5–11 (1979).
Science, vol. 196, Editorial page, Apr. 1977.
Nature 274, 398–400 (1978).
Huber et al., Can. J. Microbiol 24, 631–632 (1978).
J. Bacteriol 121, 416–421 (1975).
Biomedicine 26, 236–249 (1977).
J. Gen. Microbiol 90, 336–346 (1975).

Primary Examiner—Alvin E. Tanenholtz
Attorney, Agent, or Firm—Roman Saliwanchik

[57] ABSTRACT

A novel chemical compound, essentially pure plasmid pUC6, which is obtainable from a biologically pure culture of the microorganism Streptomyces espinosus biotype 23724a, NRRL 11439. The pUC6 plasmid is useful as a cloning vehicle in recombinant DNA work. For example, using DNA methodology, a desired gene, for example, the insulin gene, can be inserted into pUC6 and the resulting plasmid can then be transformed into a suitable host microbe which, upon culturing, produces the desired insulin.

5 Claims, 1 Drawing Figure

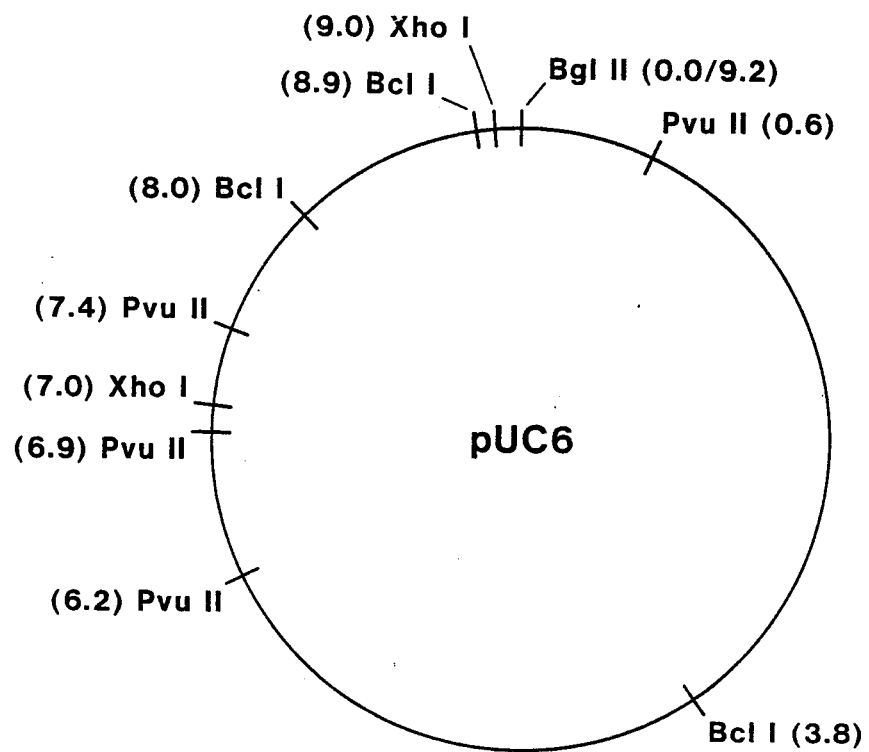

PLASMID AND PROCESS OF ISOLATING SAME

BACKGROUND OF THE INVENTION

The development of plasmid vectors useful for recombinant DNA genetics among microorganisms is well known. The editorial in Science, Vol. 196, April, 1977, gives a good summary of DNA research. This editorial is accompanied by a number of supporting papers in the same issue of Science.

Similar DNA work is currently being done on industrially important microorganisms of the genus Streptomyces. [Bibb, M. J., Ward, J. M., and Hopwood, D. A. 1978. "Transformation of plasmid DNA into Streptomyces at high frequency". Nature 274, 398–400]. Through plasmid DNA's have been detected in several Streptomycetes [Huber, M. L. B. and Godfrey, O. 1978. "A general method for lysis of Streptomyces species". Can. J. Microbiol. 24, 631–632.] [Schrempf, H., Bujard, H., Hopwood, D. A. and Goebel, W. 1975. "Isolation of covalently closed circular deoxyribonucleic acid from Streptomyces coelicolor A3(2)". J. Bacteriol. 121, 416–421.][Umezawa, H. 1977. "Microbial secondary metabolities with potential use in cancer treatment (Plasmid involvement in biosynthesis and compounds)". Biomedicine 26, 236–249.], [Malik, V. S. 1977. Preparative Method for the isolation of super-coiled DNA from a chloramphenicol producing Streptomycete. J. Antibiotics 30, 897–899.], only one Streptomycete plasmid has been physically isolated and extensively characterized in the literature [Schrempf, supra]. The existence of other plasmids in the genus Streptomyces has been inferred from reported genetic data as follows:

(1) Akagawa, H., Okanishi, M. and Umezawa, H. 1975. "A plasmid involved in chloramphenicol production in Streptomyces venezuelae: Evidence from genetic mapping". J. Gen. Microbiol. 90, 336–346.

(2) Freeman, R. F. and Hopwood, D. A. 1978. "Unstable naturally occurring resistance to antibiotics in Streptomyces". J. Gen. Microbiol. 106, 377–381.

(3) Friend, E. J. Warren, M. and Hopwood, D. A. 1978. "Genetic evidence for a plasmid controlling fertility in an industrial strain of Streptomyces rimosus". J. Gen. Microbiol. 106, 201–206.

(4) Hopwood, D. A. and Wright, H. M. 1973. "A plasmid of Streptomyces coelicolor carrying a chromosomal locus and its inter-specific transfer". J. Gen. Microbiol. 79, 331–342.

(5) Hotta, K., Okami, Y. and Umezawa, H. 1977. "Elimination of the ability of a kanamycin-producing strain to biosynthesize deoxystreptamine moiety by acriflavine". J. Antibiotics 30, 1146–1149.

(6) Kirby, R., Wright, L. F. and Hopwood, D. A. 1975. "Plasmid-determined antibiotic synthesis and resistance in Streptomyces coelicolor". Nature 254, 265–267.

(7) Kirby, R. and Hopwood, D. A. 1977. "Genetic determination of methylenomycin synthesis by the SCPI plasmid of Streptomyces coelicolor A3(2)". J. Gen. Microbiol. 98, 239–252.

(8) Okanishi. M., Ohta, T. and Umezawa, H. 1969. "Possible control of formation of aerial mycelium and antibiotic production in Streptomyces by episomic factors". J. Antibiotics 23, 45–47.

BRIEF SUMMARY OF THE INVENTION

Plasmid pUC6 is obtainable from the novel microorganism Streptomyces espinosus biotype 23724a, NRRL 11439. This plasmid can be obtained from NRRL 11439 by growing the culture on a suitable medium, fragmenting the mycelia, incubating the fragmented mycelia, harvesting the culture after a suitable time, and then lysing the mycelia. From this lysate it is possible to isolate essentially pure pUC6. Plasmid pUC6 is, advantageously small and present at many copies per cell. As such, pUC6 represents the only small high copy number plasmid described to date in Streptomyces. Further, its sensitivities to a variety of restriction endonucleases should allow its ready modification and adaptation to a number of host vector systems.

pUC6 is characterized by standard characterization tests which includes its molecular weight, approximately 6.0 megadaltons, a restriction map as shown in the drawing, and presence at 20–40 copies per *S. espinosus* NRRL 11439 cell.

pUC6 is useful as a cloning vector in DNA work wherein desired genes are incorporated into the plasmid, and the plasmid then transformed into a suitable host.

REFERENCE TO THE DRAWING

The drawing depicts the restriction endonuclease cleavage map for pUC6. The map is constructed on the basis of plasmid pUC6 having a molecular weight of ca. 6.0 megadaltons or a molecular length of ca. 9.2 kilobases. The map positions of the various restriction sites are given as kilobase coordinates relative to the Bgl II restriction site at 0.0/9.2 kilobases. The restriction endonuclease abbreviations are as follows: (1) Bgl II is an enzyme from *Bacillus globigii;* (2) Bcl I is an enzyme from *Bacillus caldolyticus;* (3) Pvu II is an enzyme from *Proteus vulgaris;* and (4) Xho I is an enzyme from *Xanthomonas holcicola*.

DETAILED DESCRIPTION OF THE INVENTION

The Microorganism pUC6 is obtainable from *Streptomyces espinosus* biotype 23724a, NRRL 11439. This biologically pure culture is available from the permanent collection of the Northern Regional Research Laboratory, U.S. Department of Agriculture, Peoria, Ill., U.S.A.

An actinomycete culture, isolated in the Upjohn soil screening laboratory from a soil sample was determined to be a biotype of the known microbe *Streptomyces espinosus* NRRL 3890. The new isolate is compared with the type culture, *S. espinosus* NRRL 3890 [Argoudelis, A. D., J. H. Coats, and T. R. Pyke. 1972. Lincomycin production. U.S. Pat. No. 3,697,380] in Tables 1–5. The biotype grows on the media cited and utilizes the carbon compounds in the synthetic media to lesser degree than the type culture. Surface or aerial growth is primarily vegetative and appears cream white. The type culture has heavy gray-green aerial growth (indicative of heavy sporulation). Small patches of gray-green sporulation are found on the biotype. An examination of the sporulation material of both strains reveals short spore chains which are straight, flexuous, or open spiral and which bear round spiny spores. Both strains are thermoduric and produce the antibiotic lincomycin. The new strain contains the plasmid pUC6. The characteristics of the new strain are sufficiently similar to those of the type strain that we consider it to be *Streptomyces espinosus*. However, the new strain can be differentiated from the type culture by properties noted in the tables. A biotype designation [Lapage, S. P., et al. eds. 1975. International Code of Nomenclature of Bacteria (Bacteriological Code, 1976 Revision). ASM, Wash., D.C.] is given to the strain to indicate its properties are not identical with those of the type culture. The designation is *Streptomyces espinosus* biotype 23724a, NRRL 11439.

Color characteristics: Aerial growth poor gray-green. Melanin negative. Appearance on Ektachrome [Dietz, A. Ektachrome transparencies as aids in actinomycete classification. Ann. N.Y. Acad. Sci. 60: 152–154.] is given in Table 2. The culture may be placed in the Green (GN) and Gray (GY) color series of Tresner and Backus [Tresner, H. D., and E. J. Backus. 1963. System of color wheels for streptomycete taxonomy. Applied Microbiol. 11: 335–338.].

Microscopic characteristics: Spores chains short, straight to flexuous, to open spiral (RF, RA) in the sense of Pridham et al. [Pridham, T. G., C. W. Hesseltine, and R. G. Benedict. 1958. A guide for the classification of streptomycetes according to selected groups. Placement of strains in morphological sections. Applied Microbiol 6: 52–79.]. Spores observed by scanning electron microscopy mostly spherical. Spore surface thorny to spiny, with appearance of transition to hairy on some spines.

Cultural and biochemical characteristics: Cultural and biochemical characteristics are cited in Table 3.

Carbon utilization: Growth of the culture on carbon compounds was determined in the synthetic medium of Pridham and Gottlieb [Pridham, T. G., and D. Gottlieb. 1948. The utilization of carbon compounds by some Actinomycetales as an aid for species determination. J. Bacteriol. 56: 107–114.] and in their modified medium [Shirling, E. B., and D. Gottlieb. 1966. Methods for characterization of Streptomyces species. International Journal of Systematic Bacteriology 16: 313–340.]. See Tables 4 and 5.

Temperature: Growth was poor at 18° C. and lacking at 55° C. It was good at 24°–45° C. Good growth at 45° C. was observed in 24–48 hours. The agar media used for temperature studies were Bennett's, Czapek's sucrose, maltose-tryptone, and Hickey-Tresner (modified).

TABLE 1

Appearance of *Streptomyces espinosus* Cultures on Ektachrome

| Agar Medium | Determination | NRRL 3890 | NRRL 11439 |
|---|---|---|---|
| Bennett's | S | Gray-green | Very slight trace white |
|  | R | Pale yellow-tan | Pale yellow-tan |
| Czapek's sucrose | S | Gray-green | Gray-green |
|  | R | Pale gray | Pale gray |
| Maltose-tryptone | S | Gray-green | Gray-green-white |
|  | R | Yellow-tan to olive | Yellow-tan |
| Peptone-iron | S | White | Pale gray-white |
|  | R | Yellow | Yellow |
| 0.1% Tyrosine | S | Colorless | Colorless |
|  | R | Red | Red |

S = Surface
R = Reverse

TABLE 2

Reference Color Characteristics of *Streptomyces espinosus* Cultures*

| Agar Medium | Determination | NRRL 3890 | | NRRL 11439 | |
|---|---|---|---|---|---|
| Bennett's | S | 127 gy. 01 G | Gray olive green | 93 y Gy to 127 gy. 01 G | Yellowish gray to gray olive green |
|  | R | 71 m. OY | Moderate orange yellow | 70 l. OY | Light orange yellow |
|  | P | 73 p. OY | Pale orange yellow | 73 p. OY | Pale orange yellow |
| Czapek's sucrose | S | 127 gy. 01 G | Gray olive green | 93 y Gy to 127 gy. 01 G | Yellowish gray to gray olive green |
|  | R | 89 p. Y | Pale yellow | 89 p. Y | Pale yellow |
|  | P | — | — | — | — |
| Maltose-tryptone | S | 127 gy. 01 G | Gray olive green | 93 y Gy to 127 gy. 01 G | Yellowish gray to gray olive green |
|  | R | 89 p. Y | Pale yellow | 70 l. OY | Light orange yellow |
|  | P | — | — | — | — |
| Hickey-Tresner (modified) | S | 93 y Gy to 127 gy. 01 G | Yellowish gray to gray olive green | 93 y Gy to 127 gy. 01 G | Yellowish gray to gray olive green |
|  | R | 70 l. OY | Light orange yellow | 70 l. OY | Light orange yellow |
|  | P | — | — | — | — |
| Yeast extract-malt extract (ISP-2) | S | 127 gy. 01 G | Gray olive green | 93 y Gy to 127 gy. 01 G | Yellowish gray to gray olive green |
|  | R | 70 l. OY | Light orange yellow | 70 l. OY | Light orange yellow |
|  | P | — | — | — | — |
| Oatmeal (ISP-3) | S | 127 gy. 01 G | Gray olive green | 93 y GY to 127 gy. 01 G | Yellowish gray to gray olive green |
|  | R | 70 l. OY | Light orange yellow | 70 l. OY | Light orange yellow |
|  | P | — | — | — | — |
| Inorganic-salts starch (ISP-4) | S | 127 gy. 01 G | Gray olive green | 93 y Gy to 127 gy. 01 G | Yellowish gray to gray olive green |
|  | R | 70 l. OY | Light orange yellow | 70 l. OY | Light orange yellow |
|  | P | — | — | — | — |
| Glycerol-asparagine (ISP-5) | S | 127 gy. 01 G | Gray olive green | 93 y Gy to 127 gy. 01 G | Yellowish gray to gray olive green |
|  | R | p. OY | Pale orange yellow | 68 s. OY | Strong orange yellow |

TABLE 2-continued

Reference Color Characteristics of *Streptomyces espinosus* Cultures*

| Agar Medium | Determination | NRRL 3890 | NRRL 11439 |
|---|---|---|---|
| | P | — | — — — |

S = Surface
R = Reverse
P = Pigment

*SP 440. Color: Universal Language and Dictionary of Names. U.S. Government Printing Office, Washington, D.C. 20402.
SRM 2106. ISCC-NBS Centroid Color Charts. Office of Standard Reference Material, Room B311, Chem. Bldg., National Bureau of Standards, Washington, D.C. 20234.
SRM 2107. Color Kit. Consists of: SRM 2106, ISCC-NBS Centroid Color Charts, and SP 440, Color: Universal Language and Dictionary of Names.

TABLE 3

Cultural and Biochemical Characteristics of *Streptomyces espinosus* Cultures

| Medium Agar | Determination | NRRL 3890 | NRRL 11439 |
|---|---|---|---|
| Peptone-iron | S | Very pale gray | Very pale gray |
| | R | Yellow-tan | Yellow-tan |
| | P | Yellow | Yellow |
| | O | Melanin-negative | Melanin-negative |
| Calcium malate | S | Very pale cream-gray-green | Very pale cream-gray-green |
| | R | Very pale cream | Very pale cream |
| | P | None | None |
| | O | Malate partially solubilized | Malate partially solubilized |
| Glucose asparagine | S | Heavy gray-green | Mottled cream-gray-green |
| | R | Gray-green-black with yellow edge | Cream-olive |
| | P | None | Pale yellow |
| Skim milk | S | Very pale gray-cream | Cream |
| | R | Orange brown | Orange-tan |
| | P | Orange-tan | Orange-tan |
| | O | Casein solubilized | Casein solubilized around growth |
| Tyrosine | S | Heavy gray-green | Gray-pink |
| | R | Dark reddish-tan-brown | Dark reddish-tan-brown |
| | P | Dark reddish-tan-brown | Dark reddish-tan-brown |
| | O | Tyrosine solubilized | Tyrosine solubilized |
| Xanthine | S | Heavy gray-green | Pink-white flecked with green |
| | R | Very pale cream-yellow | Very pale cream-yellow |
| | P | Very pale cream | Very pale cream |
| | O | Xanthine not solubilized | Xanthine not solubilized |
| Nutrient starch | S | Pale gray in center. Heavy gray-green on edge | Pink-white flecked with green |
| | R | Pale cream-yellow | Pale cream-yellow |
| | P | Very pale yellow | Very pale yellow |
| | O | Starch solubilized | Starch solubilized |
| Yeast extract-malt extract | S | Heavy gray-green | Pale gray in center. Gray-green on edge |
| | R | Pale yellow-tan | Very pale yellow |
| Gelatin | | | |
| Plain | | Trace cream aerial on surface growth | Trace cream aerial on surface growth |
| | | Yellow pigment | No pigment |
| | | Liquefaction complete | Liquefaction complete |
| Nutrient | | White aerial on surface growth | Trace cream aerial on surface growth |
| | | Yellow-tan pigment | No pigment |
| | | Liquefaction complete | Liquefaction complete |
| Broth | | | |
| Synthetic nitrate | | Slight compact bottom growth | Very slight compact bottom growth |
| Nutrient nitrate | | Surface ring and pellicle with green-gray-white aerial growth | Slight surface pellicle of colorless vegetative growth |
| Litmus milk | | Blue-gray-tan surface ring with light gram aerial growth | Blue-gray-tan surface ring with gray aerial growth |
| | | Deep purple pigment | Deep purple pigment |
| | | Peptonization | Peptonization |
| Peptone-yeast extract-iron (ISP-6) | S | Pale cream-pink | Pale cream-tan-pink |
| | R | Yellow-tan pigment | Pale yellow-tan |
| | P | Yellow-tan pigment | Pale yellow-tan |
| | O | Melanin-negative | Melanin-negative |
| Tyrosine (ISP-7) | S | Good gray-green | Mottled gray-green-cream |
| | R | Pale gray-green | Pale gray-green |
| | P | None | None |
| | O | Melanin-negative | Melanin-negative |

S = Surface
R = Reverse
P = Pigment
O = Other Characteristics

TABLE 4

Utilization Of Carbon Compounds By
*Streptomyces espinosus* Cultures in the Synthetic
Medium of Pridham And Gottlieb*

| | CONTROL | NRRL 3890 (+) | NRRL 11439 (+) |
|---|---|---|---|
| 1. | D-xylose | + | + |
| 2. | L-arabinose | + | + |
| 3. | Rhamnose | + | + |
| 4. | D-fructose | + | + |
| 5. | D-galactose | + | + |
| 6. | D-glucose | + | + |
| 7. | D-mannose | + | + |
| 8. | Maltose | + | + |
| 9. | Sucrose | (+) | (+) |
| 10. | Lactose | + | + |
| 11. | Cellobiose | + | + |
| 12. | Raffinose | (+) | (+) |
| 13. | Dextrin | + | + |
| 14. | Inulin | + | + |
| 15. | Soluble starch | + | + |
| 16. | Glycerol | + | + |
| 17. | Dulcitol | (+) | (+) |
| 18. | D-mannitol | + | + |
| 19. | D-sorbitol | (+) | (+) |
| 20. | Inositol | + | + |
| 21. | Salicin | + | (+) |
| 22. | Phenol | (−) | − |
| 23. | Cresol | − | − |
| 24. | Na formate | (+) | (−) |
| 25. | Na oxalate | (+) | (+) |
| 26. | Na tartrate | (+) | (+) |
| 27. | Na salicylate | − | − |
| 28. | Na acetate | (+) | (+) |
| 29. | Na citrate | (+) | (+) |
| 30. | Na succinate | (+) | (+) |

+ = Good utilization
(+) = Poor utilization
(−) = Doubtful utilization
− = No growth
*Pridham, T.G., and D. Gottlieb. 1948. The utilization of carbon compounds by some Actinomycetales as an aid for species determination. J. Bacteriol. 56: 107–114.

TABLE 5

Utilization Of Carbon Compounds By
*Streptomyces espinosus* Cultures in the Synthetic
Medium Of Shirling and Gottlieb*

| | NRRL 3890 | NRRL 11439 |
|---|---|---|
| CONTROL | | |
| Negative-basal medium | ± | ± |
| Positive-basal medium plus D-glucose | + | + |
| Carbon Compounds | | |
| L-Arabinose | ++ | + |
| Sucrose | − | − |
| D-Xylose | ++ | + |
| Inositol | ++ | + |
| D-Mannitol | ++ | + |
| D-Fructose | ++ | + |
| Rhamnose | ++ | + |
| Raffinose | ± | + |
| Cellulose | − | − |

++Strong utilization
±Utilization doubtful
+Positive utilization
−Utilization negative
*Shirling, E.B., and D. Gottlieb. 1966. Methods for characterization of Streptomyces species. Int. J. Syst. Bacteriol 16: 313–340.

Characteristics Of pUC6

Molecular Weight: ca. 6.0 megadaltons.
Copies Per Cell: 20–40.
Restriction Endonuclease Sensitivities:
pUC6 has the following sensitivities to restriction endonucleases. Please refer to the drawing for the restriction endonuclease cleavage map for pUC6.

| Plasmid Sensitivities To Restriction Endonucleases | | | |
|---|---|---|---|
| # Cleavage Sites | | # Cleavage Sites | |
| Enzyme | pUC6 | Enzyme | pUC6 |
| Bgl I | >7 | Bgl II | 1 |
| BamHI | 0 | Hpa I | 0 |
| Hpa II | Many | Hind III | 0 |
| EcoRI | 0 | Kpn I | 0 |
| Pst I | 0 | Pvu II | 4 |
| Mbo II | >5 | Ava I | >7 |
| Xba I | 0 | Xho I | 2 |
| Sal I | 5–6 | Sma I | >5 |
| Hinc II | >7 | | |

These results were obtained by digestion of pUC6 DNA in the presence of an excess of restriction endonuclease. The number of restriction sites were determined from the number of resolvable fragments in either 0.7 or 1.0% agarose gels.

pUC6 can be used to create recombinant plasmids which can be introduced into host bacteria by transformation. The process of creating recombinant plasmids is well known in the art. Such a process comprises cleaving the isolated vector plasmid, e.g., pUC6, at a specific site(s) by means of a restriction endonuclease, for example, Bgl II, Xho I, and the like. The plasmid, which is a circular DNA molecule, is thus converted into a linear DNA molecule by the enzyme which cuts the two DNA strands at a specific site. Other non-vector DNA is similarly cleaved with the same enzyme. Upon mixing the linear vector or portions thereof and non-vector DNAs, their single-stranded or blunt ends can pair with each other and in the presence of a second enzyme known as polynucleotide ligase can be covalently joined to form a single circle of DNA.

The above procedure also can be used to insert a length of DNA from a higher animal into pUC6. For example, the DNA which codes for ribosomal RNA in the frog can be mixed with pUC6 DNA that has been cleaved. The resulting circular DNA molecules consist of plasmid pUC6 with an inserted length of frog rDNA.

The recombinant plasmids containing a desired genetic element, prepared by using pUC6, can be introduced into a host organism for expression. Examples of valuable genes which can be inserted into host organisms by the above described process are genes coding for somatostatin, rat proinsulin, and proteases.

The usefulness of plasmid pUC6 is derived from its capacity to function as a plasmid vector in industrially important microorganisms, e.g. Streptomyces. Hence, cloning of genetic information from Streptomyces into pUC6 provides a means of increasing the production of commercially important products from these organisms, e.g. antibiotics.

This approach is compared to the concept of cloning genes for antibiotic production into the well characterized *Escherichia coli* K-12 host-vector system. The *E. coli* system has the disadvantage that it has been found that genes from some Gram-positive organisms, e.g. Bacillus, do not express well in the Gram-negative *E. coli* host. Likewise, plasmids from Gram-negative organisms are not maintained in Gram-positive hosts, and Gram-negative genetic information is either expressed poorly or not at all in Gram-positive hosts. This clearly argues for the advantage of a Gram-positive host-vector system and argues the usefulness of plasmid pUC6 in such a system.

In general, the use of a host-vector system to produce a product foreign to that host requires the introduction of the genes for the entire biosynthetic pathway of the product to the new host. As discussed above, this may lead to problems of genetic expression, but may also generate new and/or increased problems in the fermentation of the microorganisms and in the extraction and purification of the product. A perhaps more useful approach is to introduce a plasmid vector, e.g. pUC6, into a host which normally produces the product and clone onto that plasmid the genes for biosynthesis of the product. At the very least, problems of fermentation and product extraction and purification should be minimized. Additionally, in this cloning system it may not be necessary to clone and amplify all the genes of the biosynthetic pathway, but rather it may be necessary only to clone regulatory genes or genes coding for the enzymes that are rate limiting in product biosynthesis. Since pUC6 is a streptomycete plasmid, it is ideally suited for these purposes in the genus Streptomyces. Furthermore, since pUC6 is also a plasmid from a Gram-positive organism, it may serve as a vector in a number of other microorganisms, e.g. Bacillus, Arthrobacter, etc.

*Streptomyces espinosus* biotype 23724a, NRRL 11439, can be grown in an aqueous nutrient medium under submerged aerobic conditions. The organism can be grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added since tap water and unpurified ingredients are used as components of the medium prior to sterilization of the medium.

The inoculated medium can be incubated at any temperature conducive to satisfactory growth of the microorganism, for example, between about 18° and 50° C., and preferably between about 20° and 37° C. Ordinarily, optimum growth of the microorganism is obtained in about 3 to 15 days. The medium normally remains acidic during the growth cycle. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the growth of the microorganism and the attendant inefficient utilization of the equipment. Accordingly, it is desirable to produce a vegetative inoculum in a nutrient broth culture by inoculating this broth culture with an aliquot from a soil liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the growth of the microorganism so long as a good growth of the microorganism is obtained.

The following examples are illustrative of the process and products of the subject invention but are not to be construed as limiting. All percentages are by weight and all solvent mixture proportions are by volume unless otherwise noted.

EXAMPLE 1—Isolation of Plasmid pUC6 From a Biologically Pure Culture of Streptomyces espinosus, biotype 23724a, NRRL 11439

The spores from a biologically pure culture of *Streptomyces espinosus* biotype 23724a, NRRL 11439 are inoculated into 10 ml of the following Difco Antibiotic Medium No. 3 Broth (Difco Labs., Detroit, Mich.): 0.15% Beef extract; 0.15% yeast extract; 0.5% peptone; 0.1% glucose; 0.35% NaCl; 0.368% $K_2HPO_4$; 0.132% $KH_2PO_4$.

The medium has previously been sterilized in a 50 ml Erlenmeyer flask. After inoculation, the flask is incubated at 37° C. for about 36 to 48 hours on a Gump or New Brunswick rotary shaker operating at 100–250 rpm. Upon completion of the incubation, the mycelia-broth suspension in the flasks is homogenized under sterile conditions and is then mixed in a sterile 125 ml Erlenmeyer flask containing 10 ml of the above medium and also, advantageously, 68% (w/v) sucrose and 1% (w/v) glycine. The addition of sucrose and glycine facilitates the subsequent lysing of the cells. The amounts of sucrose and glycine in the medium can be varied by routine adjustments with the goal being to facilitate the subsequent lysing of the cells. The flask is then incubated further for another 36 to 48 hours at 37° C. on a Gump rotary shaker, as above. After this incubation, the mycelia are separated from the broth by low speed centrifugation, for example, at 6000×g for 15 minutes at 4° C. and decantation of the supernatant from the mycelial pellet.

The supernatant is discarded and the pellet is resuspended in 1.5 ml of an isotonic buffer containing ethylenediaminotetraacetic acid (EDTA) and sucrose, e.g. TES buffer [0.03 M tris(hydroxymethyl)aminomethane (Tris), 0.005 M EDTA and 0.05 M NaCl; pH=8.0] containing 20% (w/v) sucrose. Next, 1.5 ml of a 5 mg/ml solution of lysozyme in the same buffer is added and the mixture is incubated at 37° C. for 30 minutes with occasional mixing. Then, 1.5 ml of 0.25 M EDTA (pH=8.0) is added and this mixture is incubated 15 minutes at 37° C. Subsequently, the cell suspension is lysed by the addition of 2.5 ml of a lytic mixture, e.g. [1.0% (w/v) Brij-58 (a detergent sold by Pierce Chem. Co., Rockford, Ill.), 0.4% (w/v) deoxycholic acid, 0.05 M Tris (pH=8.0) and 0.06 M EDTA] and incubation of this mixture at 37° C. for 20 minutes. The lysate is then sheared by passing it 5–10 times through a 10 ml pipet. The sheared lysate is then digested with ribonuclease (140 μg/ml) and pronase (300 μg/ml) for an additional 20 minutes at 37° C. Alternatively, the cell-lysozyme-EDTA mixture can be digested with ribonuclease and pronase before lysis with a lytic agent such as 2% sodium dodecyl sulfate in water.

This crude lysate material is then mixed with a salt, for example, cesium chloride (preferred), and cesium sulfate, and the intercalating dye ethidium bromide to give a solution of density=1.550. This solution is centrifuged to equilibrium at 145,000×g (isopycnic density gradient centrifugation). The covalently closed circular plasmid DNA is then visible in the centrifuge tube under long wave ultraviolet (320 nm) illumination as a faint fluorescent band below the intensely fluorescent band of linear chromosomal and plasmid DNAs.

Covalently closed circular plasmid DNA is prepared for characterization by removing it from the isopycnic gradients, extracting the ethidium bromide by two treatments with one third volume of isopropyl alcohol and then dialyzing the aqueous phase against an appropriate buffer, e.g. 0.1×SSC buffer (0.015 M NaCl, 0.0015 M Na$_3$C$_6$H$_5$O$_7$.2H$_2$O; pH=7.4) to yield essentially pure pUC6.

Procedures For Characterizing And Isolating pUC6

The size of pUC6 was determined by sedimentation in neutral and alkaline sucrose gradients using an internal marker plasmid DNA having a molecular weight of approximately 9.0 megadaltons and a corresponding sedimentation value of approximately 34S. From the neutral sucrose gradients the sedimention value of pUC6 was determined to be 28.5S. The molecular weight for pUC6 was calculated from the equations by Hudson et al. [Hudson, B., Clayton, D. A. and Vinograd, J. 1968. "Complex mitochondrial DNA". Cold Spring Harbor Symp. Quant. Biol. 33, 435–442]. This molecular weight is in good agreement with that estimated from the alkaline sucrose gradients.

An estimate of pUC6 molecular weight was also obtained by electron microscopy of individual DNA molecules [Kleinschmidt, A. K. (1968). Monolayer techniques in electron microscopy of nucleic acid molecules. In "Method in Enzymology" (S. P. Colowick and N. O. Kaplan, eds.) Vol. 12B, pages 361–377. Academic Press, New York]. Plasmid pUC6 was found to have an average contour length of $3.05 \times 10^{-6}$ meters and a corresponding molecular weight of 6.0 megadaltons.

The present plasmid DNA in *Streptomyces espinosus* biotype 23724a, NRRL 11439 was determined by labeling the culture with [methyl-$^3$H]thymidine, preparing crude lysates, and centrifuging samples of the lysates in cesium chloride ethidium bromide density gradients. The gradients are fractionated, the isotopic counting performed, and the percent radioactivity in the plasmid band used to quantitate the plasmid DNA and calculate the plasmid copy number [Radloff, R., Bauer, W. and Vinograd, J. 1967. "A dye-buoyant density method for detection and isolation of closed circular duplex DNA: The closed circular DNA in HeLa cells". Proc. Nat. Acad. Sci. USA 57, 1514–1520].

Restriction Endonuclease Digestion And Agarose Gel Electrophoresis

Restriction endonucleases were obtained as commercial preparations from Miles Laboratories and New England Biolabs. Enzyme digestions were prepared in accordance with the conditions specified by the suppliers using at least a two-fold excess of endonuclease.

In some experiments plasmid DNA was digested with more than one endonuclease. Two methods were used in these experiments. In the first method, the plasmid DNA was digested first with the enzyme having the lower ionic strength requirements, and then digested with the enzyme having higher ionic strength requirements after the addition of an equal volume of 2× buffer of the second enzyme. In the second method, restriction fragments of one enzyme digest were isolated from a preparative agarose gel as described by Tanaka and Weisblum [Tanaka, T., and Weisblum, B. 1975. Construction of a colicin El-R factor composite plasmid in vitro: Means for amplification of deoxyribonucleic acid. J. Bacteriol. 121, 354–362]. The isolated restriction fragments were concentrated by ethanol precipitation and then digested with other restriction enzymes. Double digest experiments were compared with single digest experiments to ensure that no abnormal restriction patterns were obtained, i.e. no nonspecific cleavage of DNA by an enzyme occurs after altering the ionic strength of the digestion mixture.

The digested samples were applied to 0.7–1% agarose gels and were electrophoresed for 2 hours at a constant applied voltage of 10–15 v/cm of gel height. [Sharp, P. A., Sugden, J. and Sambrook, J. 1973. Detection of two restriction endonuclease activities in *Haemophilus parainfluenzae* using analytical agarose-ethidium bromide electrophoresis. Biochemistry 12, 3055–3063]. The molecular weights of restriction fragments were determined relative to the standard migration patterns of bacteriophage lambda DNA digested with enzyme Hind III [Murray, K. and Murray, N. E. 1975. Phage lambda receptor chromosomes for DNA fragments made with restriction endonuclease III of *Haemophilus influenzae* and restriction endonuclease I of *Escherichia coli*. J. Mol. Biol. 98, 551–564] or EcoRI [Helling, R. B., Goodman, H. M. and Boyer, H. W. 1974. Analysis of endonuclease R.EcoRI fragments of DNA from lambdoid bacteriophages and other viruses by agarose-gel electrophoresis. J. Virology 14, 1235–1244].

The work described herein was all done in conformity with physical and biological containment requirements specified in the NIH Guidelines.

I claim:

1. Essentially pure plasmid pUC6 which is characterized by a molecular weight of approximately 6.0 megadaltons, and a restriction endonuclease cleavage map as shown in the drawing.

2. A biologically pure culture of *Streptomyces espinosus* biotype 23724a, having the deposit accession number NRRL 11439, and which also contains about 20 to about 40 copies of plasmid pUC6 per cell.

3. A process for isolating essentially pure pUC6 from *Streptomyces espinosus* biotype 23724a, NRRL 11439, which comprises:
    (a) growing *S. espinosus* biotype 23724a, NRRL 11439, on a suitable *S. espinosus* growth medium until sufficient mycelial growth is obtained;
    (b) fragmenting said mycelia;
    (c) incubating said fragmented mycelia in a suitable growth medium, as above;
    (d) harvesting the culture after a suitable time;
    (e) lysing the harvested mycelia; and
    (f) isolating essentially pure pUC6 from the lysate.

4. A process, according to claim 3, which comprises cultivating *Streptomyces espinosus* biotype 23724a, NRRL 11439, in a nutrient medium at a temperature of about 37° C. for about 36 to 48 hours.

5. A process, according to claim 3, wherein said fragmented mycelia is incubated in a growth medium containing sucrose and glycine.

* * * * *